United States Patent [19]

Torii et al.

[11] Patent Number: 4,482,435
[45] Date of Patent: Nov. 13, 1984

[54] PROCESS FOR PREPARING THIAZOLIDINE COMPOUNDS

[75] Inventors: Sigeru Torii; Hideo Tanaka; Takashi Shiroi, all of Okayama, Japan

[73] Assignee: Otsuka Kagaku Yakuhin Kabushiki Kaisha, Osaka, Japan

[21] Appl. No.: 406,518

[22] Filed: Aug. 9, 1982

[51] Int. Cl.³ ............................................. C25B 3/00
[52] U.S. Cl. ................................ 209/73 R; 204/59 R
[58] Field of Search ........................... 204/59 R, 73 R

[56] References Cited
FOREIGN PATENT DOCUMENTS 57-29588  2/1982  Japan ................................. 204/73 R
1368232   9/1974  United Kingdom .

OTHER PUBLICATIONS

Rifi et al., Introduction to Organic Electro-Chemistry, New York, (1974), pp. 221–223.
Torii et al., Chemistry Letters, 1981, (II), 1575–1578, Nov. 1981.

*Primary Examiner*—John F. Niebling
*Attorney, Agent, or Firm*—Larson and Taylor

[57] ABSTRACT

This invention provides a process for preparing a thiazolidine compound of the formula

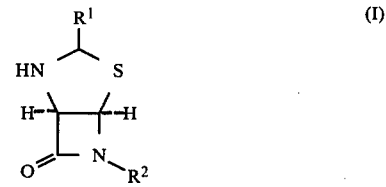

wherein $R^1$ represents a hydrogen atom, alkyl group, aralkyl group, aryl group or aryloxymethyl group, and $R^2$ represents a hydrogen atom or a group

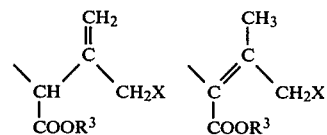

wherein $R^3$ represents a hydrogen atom, alkyl group, halogenated alkyl group, benzyl group or silyl group, and X represents a hydrogen atom, halogen atom, hydroxy group, alkoxy group or acyloxy group, the process comprising electrolyzing a thiazoline compound represented by the formula

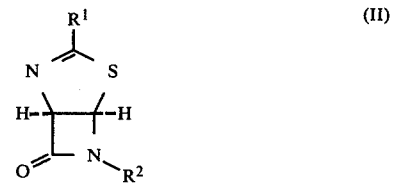

wherein $R^1$ and $R^2$ are as defined above, in a mixture comprising a perchloric acid aqueous solution and an organic solvent.

16 Claims, No Drawings

PROCESS FOR PREPARING THIAZOLIDINE COMPOUNDS

This invention relates to a novel process for preparing thiazolidine compounds, and particularly to a novel process for preparing thiazolidine compounds represented by the formula

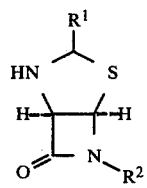
(I)

wherein $R^1$ represents a hydrogen atom, alkyl group, aralkyl group, aryl group or aryloxymethyl group, and $R^2$ represents a hydrogen atom or a group

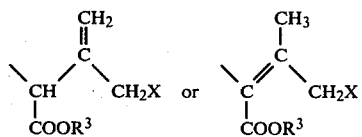

wherein $R^3$ represents a hydrogen atom, alkyl group, halogenated alkyl group, benzyl group or silyl group, and X represents a hydrogen atom, halogen atom, hydroxy group, alkoxy group or acyloxy group.

The above compounds of the formula (I) having the skeleton of 7-oxo-4-thia-2,6-diazabicyclo[3,2,0]-heptane are known to be useful as the intermediates for synthesizing physiologically active compounds such as cephalosporin derivatives, penicillin derivatives, etc. which are useful as anti-microbial agents. For example, the compound of the formula (I) can be converted to the cephalosporin derivatives of the formula (Ic) which are useful as anti-microbials, as schematically illustrated below.

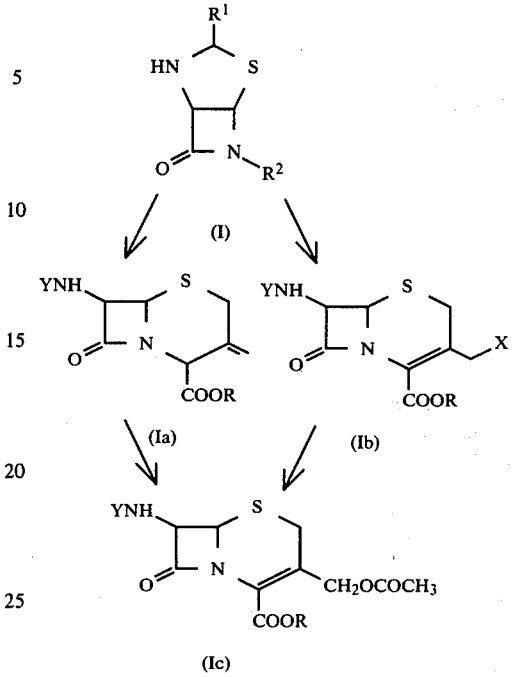

wherein Y is α-aminobenzyl-carbonyl, R is hydrogen atom, sodium or potassium metal, and X is halogen atom.

It is known to use mercury amalgam in preparing compounds of the formula (I) having the skeleton of 7-oxo-4-thia-2,6-diazabicyclo[3,2,0]-heptane by reducing the C=N double bond on the thiazoline ring of a compound having the skeleton of 7-oxo-4-thia-2,6-diazabicyclo-[3,2,0]-hept-2-ene represented by the formula

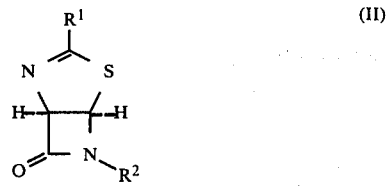
(II)

wherein $R^1$ and $R^2$ are as defined above. For example, the Specification of British Pat. No. 1,368,232 discloses a process for preparing the corresponding thiazolidine compound of the formula (I) by reducing the thiazoline compound of the formula (II). However, the conventional processes using mercury amalgam require special cares in handling toxic mercury and in disposal of waste, consequently entailing cumbersome procedures and environmental problems, and therefore undesirable as a process for mass producing the compounds of the formula (I).

It is an object of this invention to provide a process for preparing thiazolidine compounds which does not necessitate toxic mercury.

It is another object of the invention to provide a process for preparing thiazolidine compounds which is free from cumbersome procedures and environmental problems.

It is a further object of the invention to provide a process for preparing thiazolidine compounds which is suitable for mass production of the compounds.

These objects and other features of this invention will become apparent from the following description.

This invention provides a process for preparing thiazolidine compounds represented by the formula

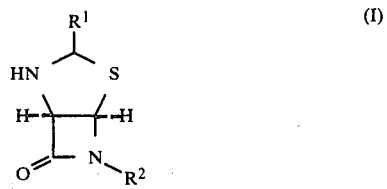 (I)

wherein $R^1$ represents a hydrogen atom, alkyl group, aralkyl group, aryl group or aryloxymethyl group, $R^2$ represents a hydrogen atom or a group

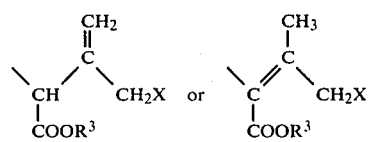

wherein $R^3$ represents a hydrogen atom, alkyl group, halogenated alkyl group, benzyl group or silyl group, and X represents a hydrogen atom, halogen atom, hydroxy group, alkoxy group or acyloxy group, the process comprising electrolyzing a compound of the formula

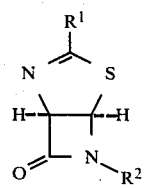 (II)

wherein $R^1$ and $R^2$ are as defined above, in the presence of a two-phase mixture comprising an aqueous solution of perchloric acid and an organic solvent.

We have conducted basic research on methods of selectively reducing the C=N double bond in the compound of the formula (II) having the skeleton of 7-oxo-4-thia-2,6-diazabicyclo[3,2,0]hept-2-ene. Consequently, we found that when the compound of the formula (II) is electrolyzed in the presence of a two-phase mixture comprising a perchloric acid aqueous solution and an organic solvent, selective reduction of the C=N double bond on the thiazoline ring takes place, giving a compound of the formula (I) having the corresponding skeleton of 7-oxo-4-thia-2,6-diazabicyclo[3,2,0]heptane in a high yield. The present invention has been accomplished based on this novel finding.

The process of this invention eliminate the need to use mercury unlike known processes, and thus is free from cumbersome procedures and environmental problems.

Furthermore, the contemplated compound of the formula (I) can be isolated with extreme ease from the reaction mixture. In addition, the perchloric acid solution and organic solvent used in the present process are usable as they are for repeated use. For these reasons, the present process is suitable for mass producing the thiazolidine compounds of the formula (I), hence advantageous.

With respect to $R^1$ in the formula (II), examples of the alkyl groups are alkyl groups having 1 to 12 carbon atoms, such as methyl, ethyl, propyl, hexyl, octyl, decyl, etc. Examples of the aralkyl groups are phenyl-substituted lower alkyl groups such as benzyl, phenethyl, phenylpropyl, etc. These aralkyl groups may have a lower alkyl group such as methyl, ethyl, etc. as a substituent on the benzene ring. Examples of the aryl groups are phenyl, tolyl, xylyl, naphthyl, etc. Examples of the aryloxymethyl groups are phenoxymethyl, tolyloxymethyl, xylyloxymethyl, naphthyloxymethyl, etc. With respect to $R^3$, examples of the alkyl groups are those having 1 to 12 carbon atoms, such as methyl, ethyl, propyl, hexyl, octyl, decyl, etc. Examples of the halogenated alkyls are alkyls having 1 to 12 carbon atoms and substituted with at least one halogen atoms. With respect to X, examples of the alkoxy groups are those having 1 to 12 carbon atoms, such as methoxy, ethoxy, propyloxy, hexyloxy, octyloxy, decyloxy, etc. Examples of the acyloxy groups are those having 2 to 10 carbon atoms, such as acetoxy, propionyloxy, butyryloxy, etc., and benzoyloxy, etc.

The compounds of the formula (II) which serve as the starting material are also known and can be prepared by a known method, for example, by allowing methyl phosphite or the like to act on the corresponding ester of penicillin-1-oxide, or by further treating the resulting compound in accordance with a conventional process.

According to this invention, the electrolysis of the starting compound is carried out in the presence of a two-phase mixture comprising a perchloric acid aqueous solution and an organic solvent. The electrolytic reaction specifically proceeds only when the aqueous solution of perchloric acid is present in the reaction system. When using an aqueous solution of any other mineral acid such as hydrogen halide, sulfuric acid, etc., no reaction takes place and the starting material is recovered, or decomposition products are given. It is preferred to use the perchloric acid aqueous solution having a concentration of about 0.1 to about 6 moles/l.

Useful organic solvents are those capable of dissolving the starting material and reaction product, and of forming a two-phase system with water. These organic solvents include a wide variety of solvents such as halogenated hydrocarbons, hydrocarbons, ethers, esters, and mixtures thereof. Among them, halogenated hydrocarbons are preferred. Examples of useful halogenated hydrocarbons are methylene chloride, chloroform, carbon tetrachloride, dichloroethane, etc. Exemplary of useful hydrocarbons are pentane, hexane, and like saturated hydrocarbons, benzene, toluene, xylene, and like aromatic hydrocarbons, etc. Examples of useful ethers are diethyl ether, ethylene glycol dimethyl ether, tetrahydrofuran, dioxane, etc. Typical of useful esters are ethyl acetate, butyl acetate, etc.

The amount of the organic solvent to be used is widely variable depending on the kind of the starting compound of the formula (II), electrolytic conditions, etc. The organic solvent is used in an amount of usually about 1 to about 10,000 parts by weight, preferably about 10 to about 1,000 parts by weight, per part by weight of the starting compound of the formula (II) in order to obtain favorable results.

The proportions of the perchloric acid aqueous solution and organic solvent are not particularly limited, and can be determined over a wide range. To give desired results, the perchloric acid aqueous solution is generally used in an amount of about 1 to about 10,000 parts by volume, preferably about 5 to about 2,000 parts by volume, per 100 parts by volume of the organic solvent.

According to this invention, usable as cathode are usual electrodes for electrolysis or metal oxide electrodes, among which electrodes of lead and of lead dioxide are preferred. As anode, various kinds of electrodes such as of lead dioxide, platinum, carbon, lead, etc. are usable.

In carrying out the process of the invention, a diaphragm may be used. However, the process need not employ a diaphragm to divide the reaction vessel into anode and cathode compartments, hence advantageous. It is preferred to carry out the electrolysis with stirring. Generally, the electrolytic reaction is conducted at a temperature of about $-10°$ to about 80° C., preferably about 0° to about 50° C. In carrying out the electrolysis of the invention, constant-applied-voltage electrolysis and controlled-potential electrolysis may be employed, but controlled-current-density electrolysis is simpler and preferable. While direct current and alternating current may be used for the electrolysis of the invention, better results are usually obtained by using direct current and alternating the direction thereof at intervals of one second to 30 minutes. Generally, the required current density ranges from about 1 to about 300 mA/cm$^2$, preferably from about 10 to about 200 mA/cm$^2$. The required electric charge is usually about 4 to about 20 F, per mole of the starting material of the formula (II). Thus the compound of the formula (I) is formed in the reaction mixture.

After the completion of the reaction, the organic layer is separated from the aqueous layer, washed with water and dried, and the solvent is distilled off. Thus using the simple procedure, the desired compound of the formula (I) can be isolated in quantitative or high yields.

The perchloric acid and organic solvent used in the process of this invention can be repeatedly used as they are. Therefore, the process of this invention is suitable for the mass production of the contemplated compounds of the formula (I), and is advantageous compared with known processes.

This invention will be described below in detail with reference to Examples.

EXAMPLE 1

Into a flask 2.2 cm in inside diameter were placed 103 mg of methyl ester of 2-(3-benzyl-7-oxo-4-thia-2,6-diazabicyclo[3,2,0]hept-2-en-6-yl)-3-methyl-3-butenoic acid. Then 2 ml of methylene chloride and 10 ml of a 10% aqueous solution of perchloric acid were introduced into the flask. A stirrer, thermometer and electrodes of lead dioxide (2×1.5 cm$^2$) were fully immersed in the mixture. Electrolysis was conducted at a current density of 20 mA/cm$^2$ and a terminal voltage of 0 to 1.2 V while maintaining the reaction temperature at 18° to 20° C. and alternating the current direction every 0.5 minutes. The electrolysis was discontinued after an electric charge of 10.8 F per mole of the starting material was passed. The methylene chloride layer was separated from the aqueous layer. The aqueous layer was then extracted with methylene chloride. The methylene chloride layer and the extract were combined, washed with water, dried and concentrated. The crude product thus obtained was purified by silica gel column chromatography, giving 96 mg of methyl ester of 2-(3-benzyl-7-oxo-4-thia-2,6-diazabicyclo[3,2,0]heptan-6-yl)-3-methyl-3-butenoic acid as white crystals. Yield: 94%.

IR(CHCl$_3$): 3635, 1760, 1743 cm$^{-1}$

NMR(CDCl$_3$): δ 1.81 (2s, 3H), 2.09 (brs, 1H), 3.20–3.30 (2d, 2H), 3.68 (s, 3H), 4.66 (s, 1H), 4.49–4.89 (1H), 4.89–5.19 (m, 3H), 5.70 (d, 1H), 7.25 (s, 5H).

EXAMPLE 2

Into a flask was placed 51.2 mg of methyl ester of 2-(3-benzyl-7-oxo-4-thia-2,6-diazabicyclo[3,2,0]hept-2-en-6-yl)-3-methyl-2-butenoic acid. Then 2 ml of methylene chloride and 10 ml of a 10% aqueous solution of perchloric acid were placed into the flask. A stirrer, thermometer and electrodes of lead deoxide (2×1.5 cm$^2$) were immersed in the mixture. Electrolysis was conducted at a current density of 20 mA/cm$^2$ and a terminal voltage of 0 to 1.2 V while maintaining the reaction temperature at 15° to 20° C. and alternating the current direction every 0.5 minute. The electrolysis was continued until an electric charge of 13.7 F per mole of the starting material was passed. A subsequent procedure similar to that of Example 1 was performed, giving 51.5 mg (quantitative yield) of methyl ester of 2-(3-benzyl-7-oxo-4-thia-2,6-diazabicyclo[3,2,0]heptan-6-yl)-3-methyl-2-butenoic acid.

IR(CHCl$_3$): 3335, 1761, 1722 cm$^{-1}$

NMR(CDCl$_3$): δ 1.90 (s, 3H), 1.80–2.10 (m, 1H), 2.18 (s, 3H), 3.24 & 3.35 (2d, 2H), 3.66 (s, 3H), 4.55–4.94 (m, 1H), 5.14 (d, 1H, J=6.0 Hz), 5.70 (d, 1H, J=6.0 Hz), 7.27 (s, 5H)

EXAMPLES 3 AND 4

A procedure similar to that of Example 1 was carried out in each of Examples 3 and 4 by using, as the starting material, methyl ester of 2-(3-benzyl-7-oxo-4-thia-2,6-diazabicyclo[3,2,0]hept-2-en-6-yl)-3-methyl-3-butenoic acid and employing the current densities and electric charges shown in Table 1 below. Table 1 shows the yields of compounds thus obtained.

TABLE 1

| Ex. | Starting material (mg) | Current density (mA/cm$^2$) | Electric charge (F/mol) | Yield (mg) |
|---|---|---|---|---|
| 3 | 334 | 30 | 4.4 | 324 (97%) |
| 4 | 408 | 20 | 6.8 | 395 (96%) |

EXAMPLE 5

A flask was charged with 53.3 mg of methyl ester of 2-(3-benzyl-7-oxo-4-thia-2,6-diazabicyclo[3,2,0]-hept-2-en-6-yl)-3-methyl-3-butenoic acid and 15.3 mg of trimethyl-hexadecane-ammonium chloride, and 0.5 ml of methylene chloride and 10 ml of a 10% perchloric acid aqueous solution. Then the flask was immersed in a supersonic washing device to form a suspension. In the suspension were dipped electrodes of lead dioxide (2×1.5 cm$^2$), a stirrer and a thermometer. Electrolysis was conducted at a current density of 20 mA/cm$^2$ and a terminal voltage of 1.1 to 1.5 V while maintaining the reaction temperature at 14° to 18° C. and alternating the current direction every 0.5 minute. The electrolysis was continued until an electric charge of 10.4 F per mole of the starting material was passed. Sodium chloride was added to the reaction mixture and the resulting mixture was vigorously agitated to separate the suspension into an aqueous layer and organic layer. Thereafter a procedure similar to that of Example 1 was carried out, giving 44.1 mg of methyl ester of 2-(3-benzyl-7-oxo-4-thia-2,6-diazabicyclo[3,2,0]heptan-6-yl)-3-methyl-3-butenoic acid. Yield: 83%.

EXAMPLE 6

Into the cathode compartment of an electrolytic bath divided by a glass diaphragm were placed 64.4 mg of methyl ester of 2-(3-benzyl-7-oxo-4-thia-2,6-diazabicyclo[3,2,0]hept-2-en-6-yl)-3-methyl-3-butenoic acid, 2 ml of methylene chloride and 11 ml of a 10% perchloric acid aqueous solution. In the anode compartment was placed a 10% aqueous solution of perchloric acid solution. Each of the anode and cathode compartments was provided with a stirrer and a electrode of lead dioxide. Electrolysis was conducted at a current density of 30 mA/cm² and a terminal voltage of 3.0 to 3.6 V while maintaining the reaction temperature at 18° to 20° C. The electrolysis was continued until an electric charge of 10.0 F per mole of the starting material was passed. Subsequently the reaction mixture in the cathode compartment was subjected to the treatments similar to those of Example 1, giving 56.5 mg of methyl ester of 2-(3-benzyl-7-oxo-4-thia-2,6-diazabicyclo[3,2,0]heptan-6-yl)-3-methyl-3-butenoic acid.

Yield: 88%.

We claim:

1. A process for preparing a thiazolidine compound represented by the formula

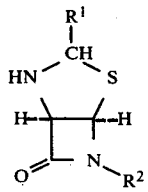

(I)

wherein $R^1$ represents a hydrogen atom, alkyl group, aralkyl group, aryl group or aryloxymethyl, $R^2$ represents a hydrogen atom or a group

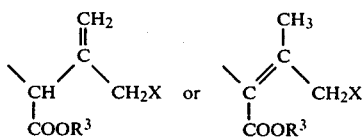

wherein $R^3$ represents a hydrogen atom, alkyl group, halogenated alkyl group, benzyl group or silyl group, and X represents a hydrogen atom, halogen atom, hydroxy group, alkoxy group or acyloxy group, the process comprising electrolyzing a thiazoline compound represented by the formula

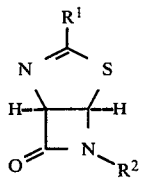

(II)

wherein $R^1$ and $R^2$ are as defined above, in a mixture comprising a perchloric acid aqueous solution and an organic solvent.

2. A process defined in claim 1 in which the organic solvent is a halogenated hydrocarbon, hydrocarbon, ether, ester or a mixture thereof.

3. A process as defined in claim 1 in which the organic solvent is a halogenated hydrocarbon.

4. A process as defined in claim 1 in which the organic solvent is used in an amount of about 1 to about 10,000 parts by weight, per part by weight of the compound of the formula (II).

5. A process as defined in claim 1 in which the organic solvent is used in an amount of about 10 to about 1,000 parts by weight per part by weight of the compound of the formula (II).

6. A process as defined in claim 1 in which the perchloric acid aqueous solution is used in a concentration of about 0.1 to about 6 moles/l.

7. A process as defined in claim 1 in which the perchloric acid aqueous solution is used in an amount of about 1 to 10,000 parts by volume per 100 parts by volume of the organic solvent.

8. A process as defined in claim 1 in which the perchloric acid aqueous solution is used in an amount of about 5 to about 2,000 parts by volume, per 100 parts by volume of the organic solvent.

9. A process as defined in claim 1 in which the electrolysis is carried out in an undivided electrolytic bath.

10. A process as defined in claim 1 in which an electrode of lead or lead dioxide is used as a cathode.

11. A process as defined in claim 1 in which the electrolysis is conducted at a temperature of about −10° to about 80° C.

12. A process as defined in claim 1 in which the electrolysis is conducted at a temperature of about 0° to about 50° C.

13. A process as defined in claim 1 in which the electrolysis is conducted while alternating the current direction at intervals of 1 second to 30 minutes.

14. A process as defined in claim 1 in which the electrolysis was carried out at a current density of about 1 to about 300 mA/cm².

15. A process as defined in claim 1 in which the electrolysis was performed at a current density of about 10 to about 200 mA/cm².

16. A process as defined in claim 1 in which an electric charge of about 4 to about 20 F per mole of the compound of the formula (II) is passed.

* * * * *